(12) United States Patent
Morrish

(10) Patent No.: US 6,192,889 B1
(45) Date of Patent: Feb. 27, 2001

(54) METHOD OF SUPPRESSION AND PREVENTION OF THE GAG REFLEX

(75) Inventor: Robert B. Morrish, Danville, CA (US)

(73) Assignee: Woodside Biomedical, Inc., Carlsbad, CA (US)

( * ) Notice: Subject to any disclaimer, the term of this patent is extended or adjusted under 35 U.S.C. 154(b) by 0 days.

(21) Appl. No.: 09/072,616

(22) Filed: May 5, 1998

(51) Int. Cl.⁷ .................................................. A61B 19/00
(52) U.S. Cl. ............................ 128/898; 128/907; 607/72
(58) Field of Search .................................... 128/898, 907; 607/72, 134, 149

(56) References Cited

U.S. PATENT DOCUMENTS

| 4,907,602 | 3/1990 | Sanders | 128/787 |
| 4,981,146 | 1/1991 | Bertolucci | 128/802 |

OTHER PUBLICATIONS

Morrish, Supression and Prevention of the Gag Reflex with a TENS Device During Dental Procedures, General Dentistry, Sep–Oct. 1997, p.498.

*Primary Examiner*—Dinh X. Nguyen
(74) *Attorney, Agent, or Firm*—K. David Crockett, Esq.; Crockett & Crockett

(57) ABSTRACT

A method for suppression and prevention of the gag reflex, particularly during dental procedures, utilizing a non-invasive nerve stimulation device applied to the wrist.

5 Claims, No Drawings

METHOD OF SUPPRESSION AND PREVENTION OF THE GAG REFLEX

FIELD OF THE INVENTION

This invention relates to suppression and prevention of the gag reflex, particularly during dental procedures.

BACKGROUND OF THE INVENTION

Most dental patients have suffered from the gag reflex when X-ray films or mold plaster is placed in the back of their mouth. As most victims know, the impulse to gag is uncontrollable and makes some dental procedures intolerable. This stimulation of the gag reflex can be a stressful time for the patient and the dentist. It can lead to delay of treatment where, for example, the patient is not able to complete X-ray or crown fitting procedures. The fear of discomfort and embarrassment from the gag reflex keeps many patients from receiving regular dental care. Still other patients are not even able to adequately perform proper oral hygiene due to gagging, even during tooth brushing.

The gag reflex starts with a noxious stimulation of the oropharynx, or back of the mouth. This palatal stimulation in turn activates the cranial Nerves V, IX, and X, causing the brain to send the gag reflex to the back of the throat. The gag reflex protects the airway and triggers the contraction of the superior laryngeal muscles.

Bertolucci, Nausea Control Device, U.S. Pat. No. 4,981,146, Jan. 1, 1991, describes a nausea control device in the form of a watch-like housing attachable to the human wrist by an adjustable attachment band. The device uses non-invasive nerve stimulation whereby electricity is passed through two electrodes to stimulate nerves located on the ventral side of the wrist (this anatomical position is sometimes referred to as the palmar side of the wrist). The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). A primary object of the invention is to provide a non-chemical, non-invasive, painless and inexpensive method of alleviating nausea. It is also portable, self-contained and convenient to the patient. Electrical pulse repetition rate of approximately 70 pulses per second and a pulse width of 80 microseconds has been found to provide effective relief of nausea in a patient. Our currently preferred electrical pulse pattern comprises about 350 microsecond pulse width at about 31 pulses per second at power levels of about 10–35 milli-amps peak pulse height. Thus a wide range of pulse patterns may be used in non-invasive nerve stimulation devices.

Sanders, Device for Controlling the Glottic Opening, U.S. Pat. No. 4,907,602, Mar. 13, 1990, describes a method of controlling the movement of the vocal cords in order to open and close the airway passage in a human subject. The method employs transcutaneous (passing or entering through the skin) or transmucosal electrical stimulation of the recurrent laryngeal nerve (RLN), which is delivered by applying electric charge from an electrode in the form of a probe or an indwelling device, to the intact neck skin at specific points along the tracheoesophageal groove or to mucosa within the esophagus, larynx, or trachea. The resulting vocal cord excursion is related to frequency of the electrical stimulus.

Where Sanders, Device for Controlling the Glottic Opening, U.S. Pat. No. 4,907,602, Mar. 13, 1990 teaches direct electrical stimulation to the nerves in the area to be affected, in that case the neck to control movement of the vocal cords, Bertolucci, Nausea Control Device, U.S. Pat. No. 4,981,146, Jan. 1, 1991, teaches indirect electrical stimulation to the nerves in the area to be affected, in that case the wrist to control nausea.

SUMMARY

The method described below employs use of the device described in Bertolucci, Nausea Control Device, U.S. Pat. No. 4,981,146, Jan. 1, 1991, and similar devices for suppression and prevention of the gag reflex, particularly during dental procedures.

DETAILED DESCRIPTION OF THE INVENTION

In Morrish, *Suppression and Prevention of the Gag Reflex with a TENS Device During Dental Procedures*, General Dentistry, September–October 1997, p498, we describe our experimental use of the device described in Bertolucci, Nausea Control Device, U.S. Pat. No. 4,981,146, Jan. 1, 1991, also known as the RELIEFBAND® NST™ non-invasive nerve stimulation device, for use in dental procedures to suppress and prevent the gag reflex. Morrish reported that a trial in the dental office environment demonstrated that the device could suppress gagging created by stimulation of the palate and hypopharynx during dental procedures in 11 of 13 patients.

Thirteen prospective dental patients with self reported histories of gagging during dental procedures volunteered for the study. The study evaluated the effectiveness of the RELIEFBAND® NST™ non-invasive nerve stimulation device in reducing gagging among these patients during dental procedures that previously had been known to produce such an effect in those patients.

Eleven subjects had the RELIEFBAND® NST™ non-invasive nerve stimulation device placed on one wrist and two patients had it placed on both wrists five to ten minutes before dental procedures were started. The RELIEFBAND® NST™ non-invasive nerve stimulation device was attached to the ventral side of the wrist such that the electro-impulses were directed at the median nerve and associated nerve structures in the area. Because the gagging response may be induced by aspiration as well as palatal stimulation, each patient who received an impression was instructed to sit up in the dental chair with his or her mouth open and to concentrate on breathing. Previously noxious oral stimulation by intra-oral impressions, intra-oral X-rays, or other dental procedures was applied.

Eleven of the thirteen patients who wore the RELIEFBAND® NST™ non-invasive nerve stimulation device during the procedure did not experience gagging. Thus, the utility of the method was established.

It is postulated that active stimulation of the A delta afferent nerve fibers has the effect of disrupting the response of cranial nerve X in the brain stem. The gate control theory attempts to explain this neural suppression or stimulation phenomena. Non-invasive nerve stimulation of ventral side of the wrist appears to stimulate the median nerve, which runs from the wrist to the brain, yet this experiment shows that it has an effect on the gag reflex which is controlled by the cranial nerves. Thus it appears that the gag reflex may be controlled by remote stimulation of the median nerve. Whatever the actual mechanism of the effect, it is clear that the non-invasive nerve stimulation of the median nerve has a mitigating effect on the gag reflex. Stimulation of the median nerve at any point along its course through the arm and neck will provide the relief which we have observed. The ventral side of the wrist is used as the most convenient spot for access to the median nerve, because it runs close to the surface of the wrist at this point. Associated nerve structures such as sensory nerves which are branches of the median nerve or run collaterally to the median nerve or communicate with the median nerve may also be effective stimulus points or areas.

While the preferred embodiments of the methods have been described in reference to the environment in which they were developed, they are merely illustrative of the principles of the inventions. Other embodiments and configurations may be devised without departing from the spirit of the inventions and the scope of the appended claims.

What is claimed is:

1. A method of suppressing or preventing the gag reflex, comprising the steps of:

mounting at least one electrode onto the ventral side of the wrist;

generating a stimulation signal; and delivering the stimulation signal to said at least one electrode to stimulate the ventral side of the wrist to suppress or prevent the gag reflex.

2. The method of claim 1 wherein said mounting step includes providing a wristwatch-like housing carrying the electrodes, and providing securing means for mounting the housing onto the wrist, with the housing having a circuit means for generating the stimulation signal encased within the housing.

3. The method of claim 1 wherein said delivering step comprises delivering an intermittent stimulation signal.

4. The method of claim 1 wherein said delivering step comprises delivering a continuous stimulation signal.

5. A method of suppressing or preventing the gag reflex, comprising the steps of:

mounting a non-invasive nerve stimulation device onto the wrist;

generating an electrical stimulation signal; and delivering the electrical stimulation signal to the wrist.

* * * * *